United States Patent
Ebinuma et al.

(10) Patent No.: US 11,702,688 B2
(45) Date of Patent: Jul. 18, 2023

(54) METHOD FOR DETECTING GENE MUTATION

(71) Applicant: SEKISUI MEDICAL CO., LTD., Tokyo (JP)

(72) Inventors: Hiroyuki Ebinuma, Tokyo (JP); Katsura Uchida, Tokyo (JP); Yuriko Tsukamoto, Tokyo (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 675 days.

(21) Appl. No.: 16/086,144

(22) PCT Filed: Mar. 29, 2017

(86) PCT No.: PCT/JP2017/012820
§ 371 (c)(1),
(2) Date: Sep. 18, 2018

(87) PCT Pub. No.: WO2017/170644
PCT Pub. Date: Oct. 5, 2017

(65) Prior Publication Data
US 2019/0032123 A1 Jan. 31, 2019

(30) Foreign Application Priority Data

Mar. 31, 2016 (JP) ................................. 2016-071361
Sep. 20, 2016 (JP) ................................. 2016-182728

(51) Int. Cl.
| | | |
|---|---|---|
| C12Q 1/68 | (2018.01) | |
| C12Q 1/6858 | (2018.01) | |
| C12N 15/00 | (2006.01) | |
| C12N 15/09 | (2006.01) | |
| C12Q 1/6886 | (2018.01) | |
| C12Q 1/6806 | (2018.01) | |
| C12Q 1/6876 | (2018.01) | |

(52) U.S. Cl.
CPC ........... *C12Q 1/6858* (2013.01); *C12N 15/00* (2013.01); *C12N 15/09* (2013.01); *C12Q 1/68* (2013.01); *C12Q 1/6806* (2013.01); *C12Q 1/6876* (2013.01); *C12Q 1/6886* (2013.01); *C12Q 2600/156* (2013.01); *C12Y 207/07007* (2013.01)

(58) Field of Classification Search
CPC ................................ C12Q 1/6858; C12Q 1/68
See application file for complete search history.

(56) References Cited

U.S. PATENT DOCUMENTS

| | | | |
|---|---|---|---|
| 7,297,496 B2 | 11/2007 | Yaku et al. | |
| 2003/0148301 A1* | 8/2003 | Aono | C12Q 1/6858 435/287.2 |
| 2003/0203381 A1 | 10/2003 | Kambara et al. | |
| 2007/0042393 A1 | 2/2007 | Yaku et al. | |
| 2012/0202199 A1* | 8/2012 | Komori | C12Q 1/6858 435/6.12 |

FOREIGN PATENT DOCUMENTS

| | | |
|---|---|---|
| CN | 104862401 A | 8/2015 |
| EP | 1241266 A1 | 9/2002 |
| JP | 2003-310300 A | 11/2003 |
| JP | 2005-160430 A | 6/2005 |
| JP | 3937136 B2 | 6/2007 |
| JP | 2010-35532 A | 2/2010 |
| WO | WO 01/42498 A1 | 6/2001 |
| WO | WO 2007/020708 A1 | 2/2007 |

OTHER PUBLICATIONS

Ishiguro et al. (2005), "High-throughput detection of multiple genetic polymorphisms influencing drug metabolism with mismatch primers in allele-specific polymerase chain reaction", Analytic Biochem 337: 256-261 (Year: 2005).*
Zhang et al., "Role of EGFR SNPs in survival of advanced lung adenocarcinoma patients treated with Gefitinib", (2013) Gene 517: 60-64 (Year: 2013).*
Winter et al., "Polymerase Chain Reaction (PCR)", (2005) eLS: 1-5 (Year: 2005).*
Liu et al; Plant Methods, vol. 8, 2012, pp. 1-9.*
Office Action dated Nov. 19, 2020 in corresponding Korean Patent Application No. 10-2018-7031013, with English translation.
English translation of the International Search Report (form PCT/ISA/210), dated May 30, 2017, for International Application No. PCT/JP2017/012820.
Japanese Office Action, with a drafting date of Feb. 21, 2018, for Japanese Application No. 2017-549546, with an English machine translation.
Japanese Office Action, with a drafting date of Nov. 24, 2017, for Japanese Application No. 2017-549546, with an English machine translation.
Thress et al., "Acquired EGFR C797S Mutation Mediates Resistance to AZD9291 in Non-small Cell Lung Cancer Harboring EGFR T790M," Nature Medicine, vol. 21, No. 6, Jun. 2015 (published online May 4, 2015), pp. 560-564.

(Continued)

*Primary Examiner* — Jehanne S Sitton
(74) *Attorney, Agent, or Firm* — Birch, Stewart, Kolasch & Birch, LLP

(57) ABSTRACT

An object of the present invention is to provide a novel method for designing a primer ensuring reactivity and discriminatory power in a method for detecting a single base substitution based on an ASP-PCR method and to provide a method for easily detecting multiple point mutations within overlapping amplicons, particularly, two adjacent single base substitutions. The single base substitutions can easily be detected by using a mutant primer in which the base of the third nucleotide from the 3' end corresponds to the base of a mutant nucleotide of a single base substitution contained in a nucleic acid sample, in which the base of the second nucleotide from the 3' end is not complementary to the base of the corresponding nucleotide of the nucleic acid, and in which the bases of the other nucleotides are complementary to the bases of the corresponding nucleotides of the nucleic acid.

3 Claims, 5 Drawing Sheets

Specification includes a Sequence Listing.

(56) References Cited

OTHER PUBLICATIONS

Yoshino et al., "Clinical Validation of a Multiplex Kit for RAS Mutations in Colorectal Cancer: Results of the RASKET (RAS KEy Testing) Prospective, Multicenter Study," EBioMedicine, vol. 2, 2015 (Published online Feb. 14, 2015), pp. 317-323.
International Preliminary Report on Patentability (Forms PCT/IB/338 and PCT/IPEA/409), dated Oct. 4, 2018, for International Application No. PCT/JP2017/012820.
Extended European Search Report, dated Aug. 21, 2019, for European Application No. 17775181.5.
Lang et al., "Optimized Allele-Specific Real-Time PCR Assays for the Detection of Common Mutations in KRAS and BRAF,"The Journal of Molecular Diagnostics, vol. 13, No. 1, Jan. 1, 2011, XP055064367, pp. 23-28.
Zhang et al., "A Novel Multiplex Tetra-Primer ARMS-PCR for the Simultaneous Genotyping of Six Single Nucleotide Polymorphisms Associated with Female Cancers," PLOS ONE, vol. 8, No. 4, Apr. 17, 2013, XP055383308, 8 pages.
Chinese Office Action and Search Report for Chinese Application No. 201780025043.7, dated Jul. 5, 2021, with an English translation.
Chinese Office Action for Chinese Application No. 201780025043.7, dated Jan. 28, 2022, with English translation.

\* cited by examiner

[FIG. 1]
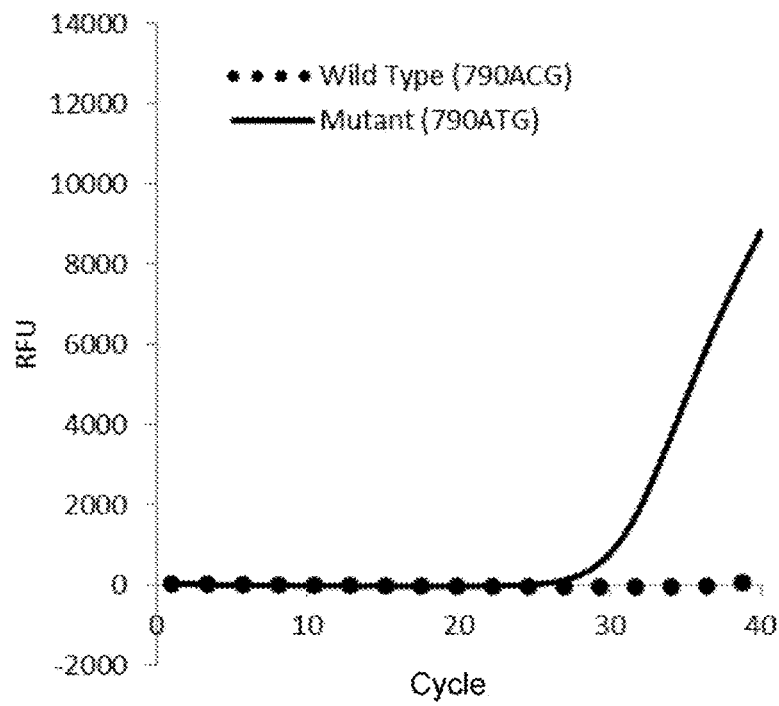
[FIG. 2]
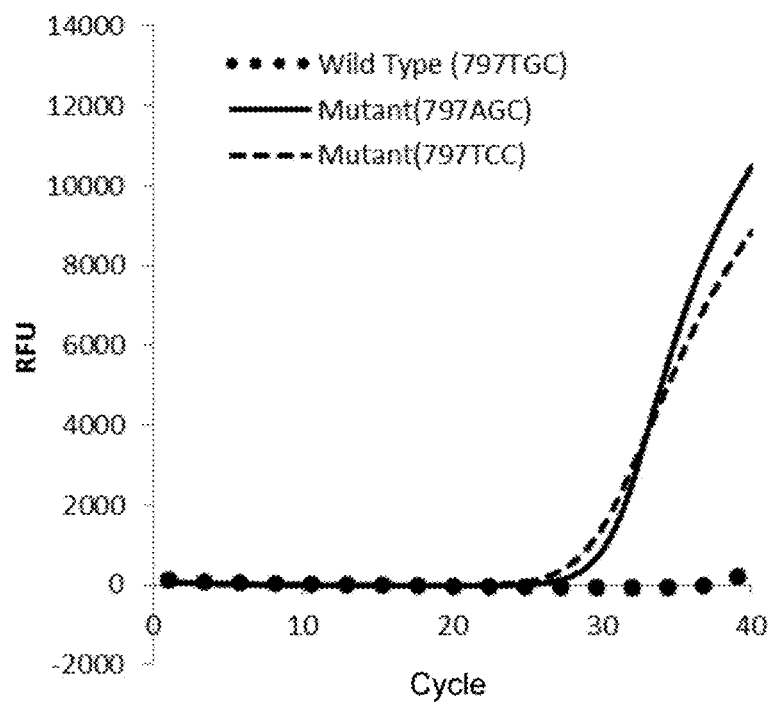

[FIG. 3]
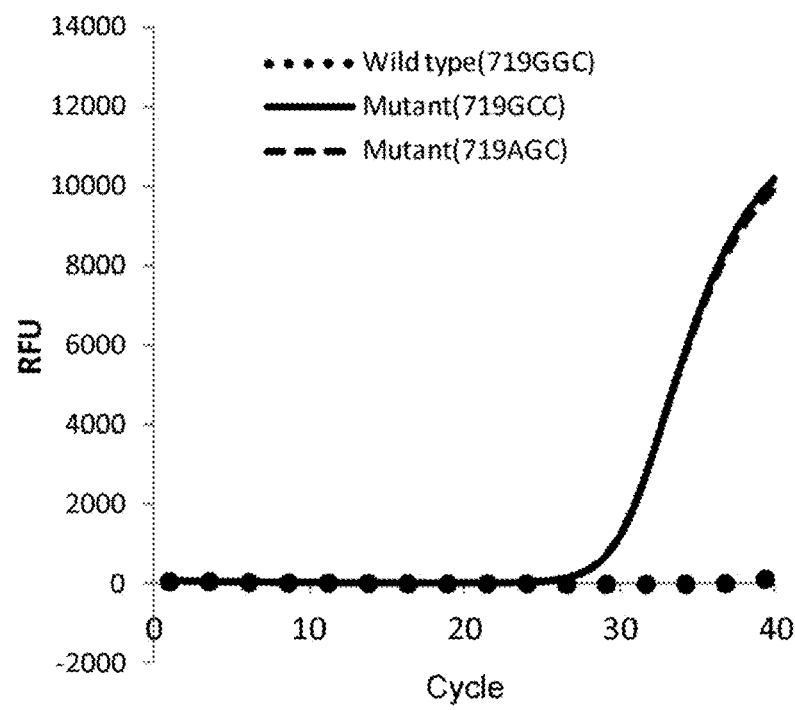
[FIG. 4]
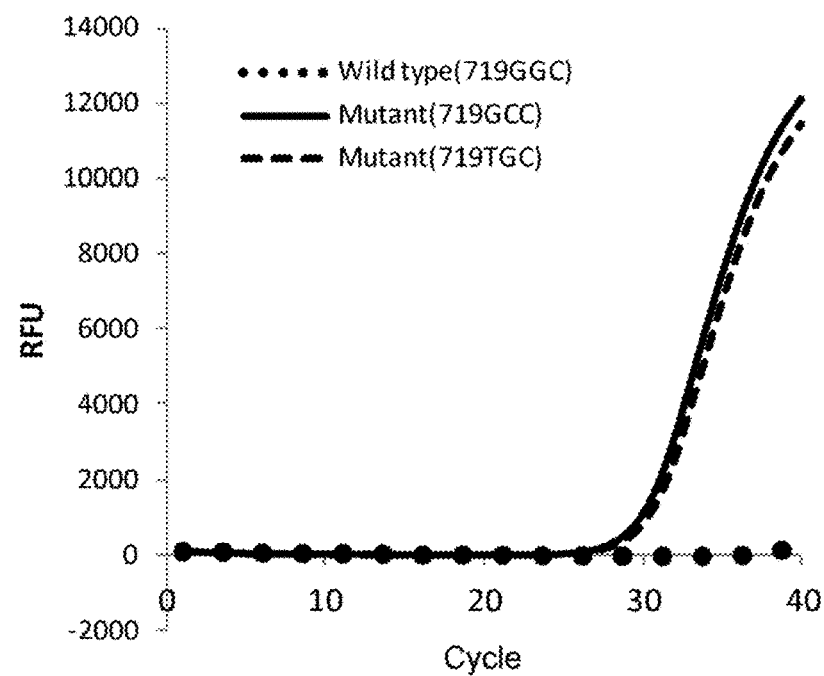

[FIG. 5]
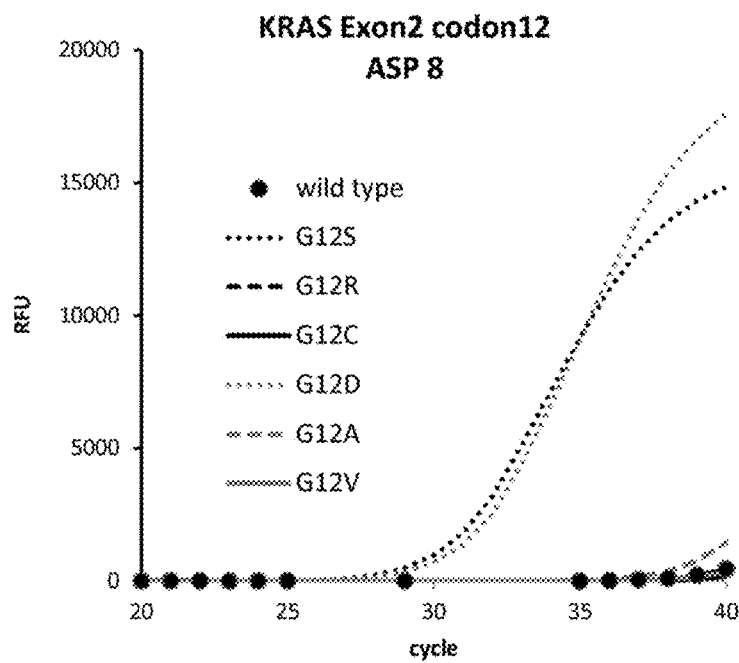
[FIG. 6]
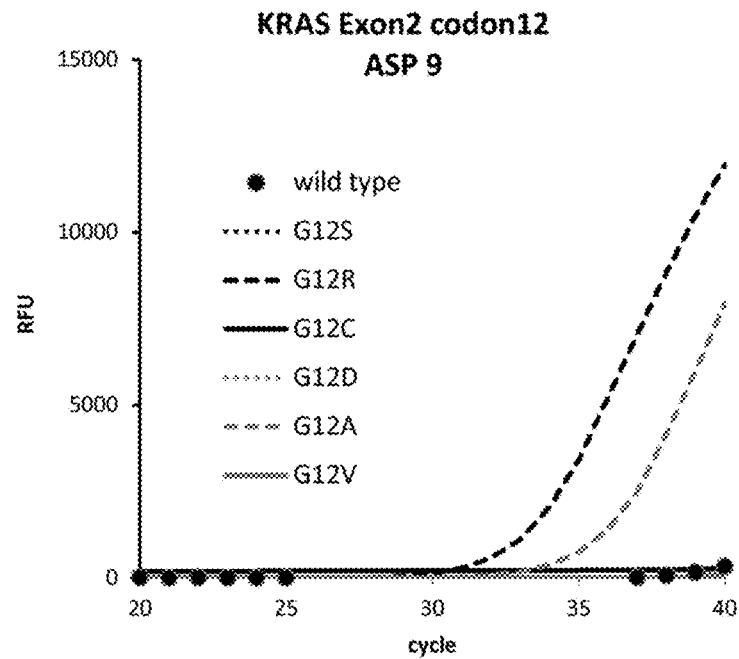

[FIG. 7]
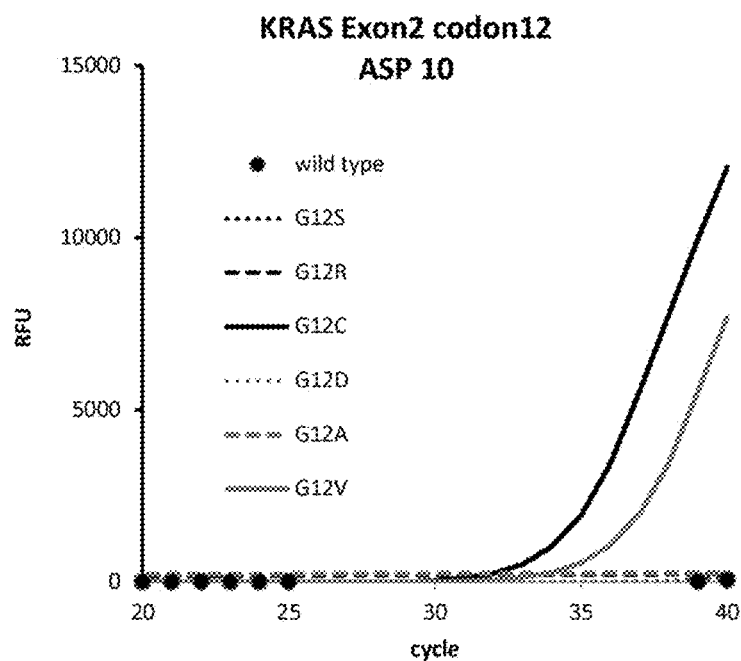
[FIG. 8]
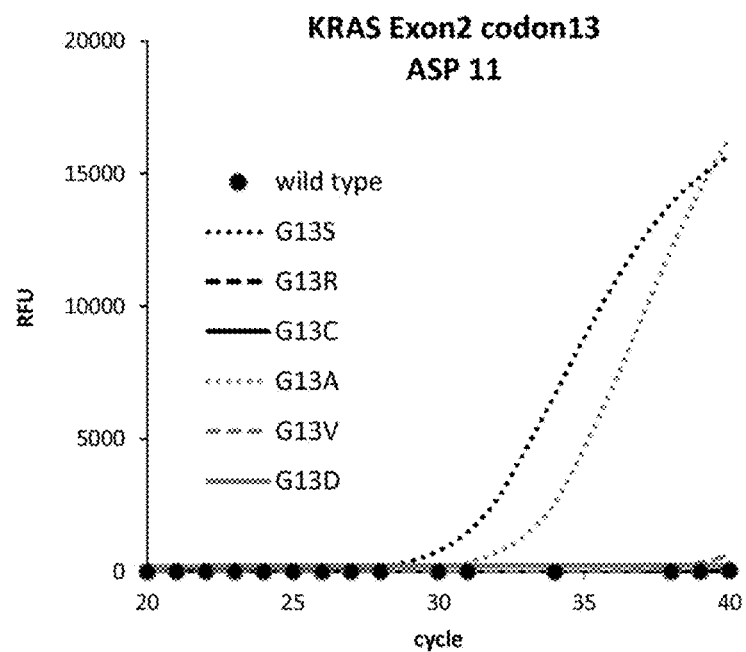

[FIG. 9]
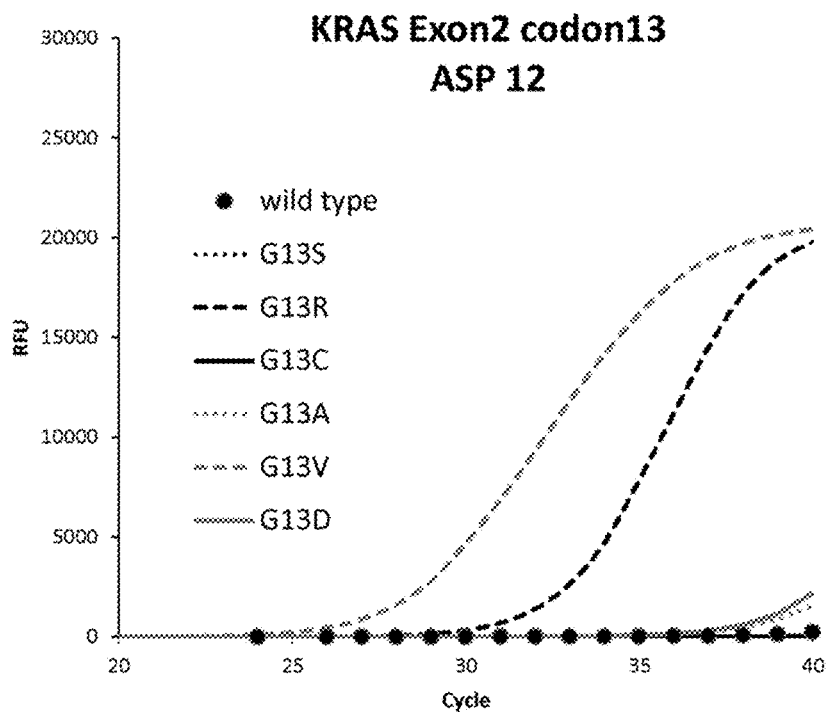
[FIG. 10]
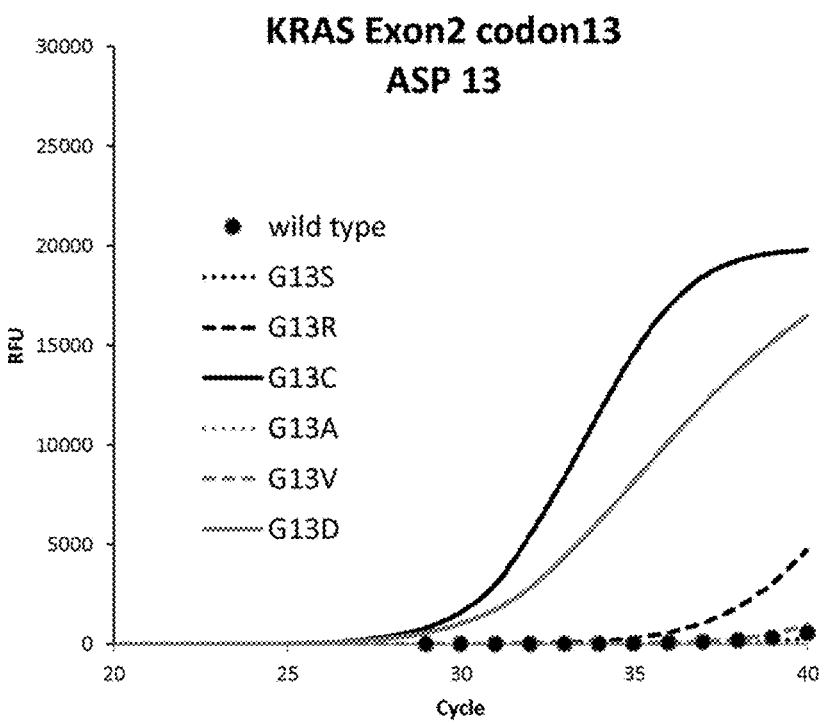

METHOD FOR DETECTING GENE MUTATION

TECHNICAL FIELD

The present invention relates to a method for specifically detecting a certain single nucleotide polymorphism (SNP) or point mutation contained in a nucleic acid sample.

Genetic mutations include a genetically inherited germline mutation and a somatic mutation that is acquired and induced in each cell, and it is reported that a certain single nucleotide polymorphism (SNP) of a certain gene among germline mutations and a point mutation (single nucleotide mutation), which is representative somatic mutation, are associated with various kinds of diseases, and in recent years, detection of these mutations is used for screening patients for which a certain drug is expected to be effective.

For example, it is found that no therapeutic effect is expected from an anti-EGFR antibody used as a therapeutic agent for colon cancer when a point mutation is found in the exon 2, 3, 4 regions of the patient's KRAS gene and NRAS gene, and a kit is developed for enabling detection of RAS (KRAS/NRAS) gene mutations associated with a total of 48 amino acid substitutions at codons 12, 13, 59, 61, 117, and 146 of KRAS gene and NRAS gene (Non-Patent Document 1). The point mutations in RAS are characterized by the variety of positions of point mutations at each codon composed of three bases, and it is required to detect an extremely large number of types of single base substitutions.

An EGFR gene mutation test is performed for judging the efficacy of a tyrosine kinase inhibitor (TKI) that is a therapeutic agent for lung cancer. EGFR gene mutationa are characterized in that various forms mutations such as deletions, insertions, and point mutations etc. are found. Among several point mutations, point mutations occurring at codon 719 in exon 18 cause substitution of the 2155th base G with A or T, or the 2156th base G with C, resulting in three types of amino acid substitutions. While TKI resistance is imparted when the 2369th base C is substituted with T at codon 790 in exon 20 of EGFR gene, a point mutation at codon 797 in exon 20 is recently newly reported as a gene mutation imparting resistance to the third generation TKI (Non-Patent Document 2) and has two forms of point mutations causing substations of the 2389th base T with A, or the 2390th base G with C.

As described above, for some of the RAS gene or EGFR gene mutations, it is required to deal with the detection of single base substitutions in the case of occurrence of two or more point mutations in one codon, and a mutation detection method is desirably as simple as possible and capable of ensuring discriminatory power.

A representative method for discriminating such a single base substitution is an ASP-PCR method in which an allele specific primer (ASP) is combined with a polymerase chain reaction method (PCR). The ASP is generally designed such that a nucleotide at 3' end of a primer corresponds to a mutated (or wild-type) nucleotide of SNP, and the 3' end hybridizes with a mutated (or wild-type) template so that elongation proceeds, while the 3' end does not hybridize with a wild-type (or mutated) template so that the elongation does not proceed. The presence/absence of single base substitution is judged depending on whether an amplification product resulting from the ASP is obtained.

However, to ensure discriminatory power by a difference of only one nucleotide at the 3' end, it is necessary to extremely strictly control a temperature condition etc. during reaction. Therefore, primer design methods have been devised. For example, a method is disclosed for conveniently and accurately detecting a single base substitution by using a detection primer having at the 3' end a base complementary to the particular base to be tested in the test nucleic acid sample, the base at the second base from the 3' end being complementary to the base of the test nucleic acid, and at least one base upstream of the third base from the 3' end being substituted with a base (artificial mismatch) different from the base complementary to the base of the test nucleic acid (Patent Document 1). Furthermore, a technique is disclosed for enabling easy and unambiguous determination by using a wild-type primer in which the second base from the 3' end of the wild-type primer corresponds to the expected wild-type nucleotide of a single nucleotide polymorphism site, in which one of bases from the third base of the 3' end to the 5' end of the primer may be substituted with a base not complementary to the base of the strand to be hybridized with the primer in the chromosome or a fragment thereof, and in which the other bases in the primer are complementary to bases of the strand to be hybridized with the primer in the chromosome or a fragment thereof, as well as a mutant primer in which the second base from the 3' end of the mutant primer corresponds to the expected mutant nucleotide of a single nucleotide polymorphism site, in which one of bases from the third base of the 3' end to the 5' end of the primer may be substituted with a base not complementary to the base of the strand to be hybridized with the primer in the chromosome or a fragment thereof, and in which the other bases in the primer are complementary to bases of the strand to be hybridized with the primer in the chromosome or a fragment thereof (Patent Document 2).

However, in the method of Patent Document 1, it is required to use a capture oligonucleotide probe having a sequence complementary to a base sequence including an artificial mismatch generated by primer elongation, and in the method of Patent Document 2, it is required to use a wild-type primer and one or two kinds of mutant primers. Since an ASP is in principle designed in accordance with the mutation of each base, a large number of primers must be prepared as the number of single base substitutions desired to be detected increases, and if two or more point mutations occur in one codon as in some of the RAS gene or EGFR gene mutations, the kinds of primers to be designed inevitably increase in number. Therefore, the method of Patent Document 1 requiring a capture oligonucleotide probe and the method of Patent Document 2 requiring a total of two or three kinds of wild-type and mutant primers cause concern about increased cost of the mutation detection reagent in some cases. Therefore, a method for designing a new primer satisfying both convenience and discriminatory power is required.

CITATION LIST

Patent Literature

Patent Document 1: Japanese Laid-Open Patent Publication No. 2005-160430
Patent Document 2: Japanese Patent No. 3937136

Non Patent Literature

Non-Patent Document 1: Yoshino T, Muro K, Yamaguchi K, Nishina T, Denda T, Kudo T, Okamoto W, Taniguchi H, Akagi K, Kajiwara T, Hironaka S, Satoh T. Clinical Validation of a Multiplex Kit for RAS Mutations in Colorectal Cancer: Results of the RASKET (RAS KEy Testing) Prospective, Multicenter Study. EBioMedicine. 2015 Feb. 14; 2(4):317-23.

Non-Patent Document 2: Thress K S, Paweletz C P, Felip E, Cho B C, Stetson D, Dougherty B, Lai Z, Markovets A, Vivancos A, Kuang Y, Ercan D, Matthews S E, Cantarini M, Barrett J C, Jaenne P A, Oxnard G R. Acquired EGFR C797S mutation mediates resistance to AZD9291 in non-small cell lung cancer harboring EGFR T790M. Nat Med. 2015 June; 21(6):560-2.

SUMMARY OF INVENTION

Technical Problem

An object of the present invention is to provide a method for designing a new primer ensuring reactivity and discriminatory power in a method for detecting a single base substitution based on an ASP-PCR method, as well as a method for easily detecting multiple point mutations within overlapping amplicons, particularly, single base substitutions of two adjacent single nucleotide polymorphism sites, for solving the problem.

Solution to Problem

The present invention has the following configurations [1] to [7].

[1] A method for detecting a single base substitution at a single nucleotide polymorphism site contained in a nucleic acid sample by utilizing a nucleic acid amplification reaction, the method combines the steps of:

(a) hybridizing to the nucleic acid a mutant primer in which the base of the third nucleotide from the 3' end corresponds to the base of a mutant nucleotide of the single nucleotide polymorphism, in which the base of the second nucleotide from the 3' end is not complementary to the base of the corresponding nucleotide of the nucleic acid, and in which the bases of the other nucleotides are complementary to bases of the corresponding nucleotides of the nucleic acid;

(b) elongating the mutant primer with a DNA polymerase and deoxyribonucleoside triphosphate that is a substrate thereof; and (c) detecting the single base substitution contained in the nucleic acid sample based on whether the mutant primer is elongated or not.

[2] The method for detecting a single base substitution according to [1] above, wherein the single nucleotide polymorphism site is a first and a second adjacent single nucleotide polymorphism sites, and wherein the step (a) is a step of hybridizing to the nucleic acid a mutant primer in which the base of the third nucleotide from the 3' end corresponds to the base of a mutant nucleotide of the first single nucleotide polymorphism, in which the base of the second nucleotide from the 3' end is not complementary to the base of the corresponding nucleotide of the nucleic acid having a mutant nucleotide of the first single nucleotide polymorphism, in which the base of the second nucleotide from the 3' end corresponds to the base of a mutant nucleotide of the second single nucleotide polymorphism, in which the base of the third nucleotide from the 3' end is not complementary to the base of the corresponding nucleotide of the nucleic acid having a mutant nucleotide of the second single nucleotide polymorphism, and in which the bases of the other nucleotides are complementary to the bases of the corresponding nucleotides of the nucleic acid.

[3] The method for detecting a single base substitution according to [1] or [2] above, wherein the single base substitution is a single base substitution of EGFR gene, KRAS gene, or NRAS gene.

[4] The method according to any one of [1] to [3] above, wherein the nucleic acid amplification reaction is a polymerase chain reaction.

[5] The method according to [4] above, wherein whether the mutant primer is elongated or not is determined based on the presence or absence of an amplification product of the polymerase chain reaction.

[6] A reagent containing a mutant primer for use in a method for detecting a single base substitution of a single nucleotide polymorphism site contained in a nucleic acid sample by utilizing a nucleic acid amplification reaction, the reagent containing a mutant primer in which the base of the third nucleotide from the 3' end corresponds to the base of a mutant nucleotide of the single nucleotide polymorphism, in which the base of the second nucleotide from the 3' end is not complementary to the base of the corresponding nucleotide of the nucleic acid, and in which the bases of the other nucleotides are complementary to the bases of the corresponding nucleotides of the nucleic acid.

[7] The reagent according to [6] above, wherein the mutant primer amplifies a mutant allele of EGFR gene, KRAS gene, or NRAS gene.

[8] The reagent according to [6] or [7] above, wherein the nucleic acid amplification reaction is a polymerase chain reaction.

[9] A method for amplifying a fragment of nucleotides comprising the steps of:

(i) hybridizing a first primer and a second primer to a deoxyribonucleic acid (DNA) molecule containing a single nucleotide polymorphism site in a sample;

(ii) elongating the first primer and the second primer with a DNA polymerase in the presence of deoxyribonucleoside triphosphate;

(iii) hybridizing the second primer to the elongated first primer and hybridizing the first primer to the elongated second primer;

(iv) elongating the second primer hybridized to the elongated first primer and the first primer hybridized to the elongated second primer in the presence of deoxyribonucleoside triphosphate with a DNA polymerase; and (v) optionally repeating the steps (iii) and (iv) once to 50 times, preferably 5 to 45 times, 10 to 45 times, 10 to 40 times, 10 to 35 times, 15 to 35 times, 20 to 35 times, or 25 to 35 times, wherein the nucleotide sequence of the first primer is complementary to one strand of the DNA molecule, the base of the third nucleotide from the 3' end corresponding to the base characterizing one genotype of the single nucleotide polymorphism, whereas the second base from the 3' end is not complementary to the base of the corresponding nucleotide of the DNA strand, wherein the nucleotide sequence of the second primer is complementary to the other strand of the DNA molecule, and wherein when hybridized to the deoxyribonucleic acid (DNA) molecule containing the single nucleotide polymorphism site in the sample, the 3' ends of the first primer and the second primer are each located on the 3' side viewed from the 3' ends of the other primers.

[10] The method for amplifying a fragment of nucleotides according to [9] above, wherein the single nucleotide polymorphism site is a first and a second adjacent single nucleotide polymorphism sites, and wherein the nucleotide sequence of the first primer is complementary to one strand of the DNA molecule, the base of the third nucleotide from the 3' end corresponding to the base characterizing one genotype of the first single nucleotide polymorphism, whereas the second base from the 3' end is not complementary to the base of the corresponding nucleotide of the DNA strand, and the base of the second nucleotide from the 3' end corresponding to the base characterizing one genotype of the second single nucleotide polymorphism, whereas the third base from the 3' end is not complementary to the base of the corresponding nucleotide of the DNA strand.

Advantageous Effects of Invention

The present invention provides a method for detecting a base sequence, or particularly, detecting a single base substitution, and enables provision of a detection method, a detection reagent, and a kit having remarkable effects such as an ability to inexpensively, easily, and accurately detect a large number of specimens efficiently without requiring a special device and an equipment for detection.

The present invention provides a method for designing a novel ASP ensuring reactivity and discriminatory power, and combines the method with a conventional ASP design method to enable provision of a method for detecting multiple point mutations within overlapping amplicons, particularly, single base substitutions of two adjacent single nucleotide polymorphism sites, by using a minimum number of the ASP.

BRIEF DESCRIPTION OF DRAWINGS

FIG. 1 shows the result of selective amplification of a PCR product from DNA containing T790M mutation in exon 20 of EGFR gene.

FIG. 2 shows the result of selective amplification of a PCR product from DNA containing C797S mutation in exon 20 of EGFR gene.

FIG. 3 shows the result of selective amplification of a PCR product from DNA containing G719A mutation and G719S mutation in exon 18 of EGFR gene.

FIG. 4 shows the result of selective amplification of a PCR product from DNA containing G719A mutation and G719C mutation in exon 18 of EGFR gene.

FIG. 5 shows the result of selective amplification of a PCR product from DNA containing G12S and G12D mutations at codon 12 in exon 2 of KRAS gene.

FIG. 6 shows the result of selective amplification of a PCR product from DNA containing G12R and G12A mutations at codon 12 in exon 2 of KRAS gene.

FIG. 7 shows the result of selective amplification of a PCR product from DNA containing G12C and G12V mutations at codon 12 in exon 2 of KRAS gene.

FIG. 8 shows the result of selective amplification of a PCR product from DNA containing G13S and G13A mutations at codon 13 in exon 2 of KRAS gene.

FIG. 9 shows the result of selective amplification of a PCR product from DNA containing G13R and G13V mutations at codon 13 in exon 2 of KRAS gene.

FIG. 10 shows the result of selective amplification of a PCR product from DNA containing G13C and G13D mutations at codon 13 in exon 2 of KRAS gene.

DESCRIPTION OF EMBODIMENTS

The present invention relates to a method for detecting a single base substitution by hybridizing a mutant primer to a target nucleic acid in a nucleic acid sample and selectively amplifying only a DNA sequence including a single base substitution.

The nucleic acid sample is not particularly limited as long as the sample contains a nucleic acid. The nucleic acid sample may be a sample containing extracted or synthesized nucleic acid or a biological sample containing various body fluids such as blood and spinal fluid, mucosa, tissues such as hair, and cells derived therefrom, or may be a sample containing individual organisms themselves such as single cell organisms and microorganisms. The origins of these nucleic acids are not limited, and nucleic acids derived from any biological and virus species are usable. The nucleic acids may be nucleic acids in the cell nuclei or extranuclear nucleic acids retained by organelles represented by mitochondria, chloroplast, nucleolus, etc. Furthermore, artificially synthesized nucleic acids or plasmids or viral vectors commonly used as vectors may be used.

The type of nucleic acid may be either DNA or RNA. In the case of DNA, various generally known DNA are usable, and genomic DNA and DNA obtained by reverse transcription of mRNA such as complementary DNA (cDNA) may also be used. For RNA, various RNAs such as generally known mRNA, rRNA, and viral RNA are usable.

Although the method used for nucleic acid amplification in the present invention is not particularly limited, the nucleic acid amplification can be performed by a conventionally known method and can be performed by a generally known PCR method etc.

The nucleic acid sequence to be amplified is not particularly limited. Any sequence can be amplified as long as the sequence is a nucleic acid sequence, and both DNA and RNA can be amplified. A nucleic acid derived from an organism can be amplified, and its species is not particularly limited. A region corresponding to an ORF (open reading frame) as well as the other portions are amplifiable. Preferably, the nucleic acid derived from a living body includes a region in which a single nucleotide polymorphism due to mutation of one or more nucleotides is identified. More preferably, the nucleic acid derived from a living body includes a region in which two adjacent single nucleotide polymorphism sites are identified. Furthermore, preferably, the nucleic acid derived from a living body includes a DNA region containing a single nucleotide polymorphism of EGFR gene, KRAS gene, or NRAS gene of the human species. The DNA region containing a single nucleotide polymorphism of EGFR gene is preferably a DNA region containing any one or more of codons 719, 790, and 797. The DNA region containing a single nucleotide polymorphism of KRAS gene is preferably a DNA region containing any one or more of codons 12, 13, 59, 61, 117, and 146. The DNA region containing a single nucleotide polymorphism of NRAS gene is preferably a DNA region containing any one or more of codons 12, 13, 59, 61, 117, and 146.

The mutant primer used in the present invention is not particularly limited as long as the primer can be used in an ordinary PCR. In the sequence of the mutant primer, the base of the third nucleotide from the 3' end is complementary to the base of a mutant nucleotide of the single nucleotide polymorphism site of the strand of a target nucleic acid to be hybridized with the primer, and the second base from the 3' end is substituted with a base that is not complementary to the corresponding base of the strand of the target nucleic acid to be hybridized with the primer, while the other bases are complementary to the corresponding bases of the strand of the target nucleic acid to be hybridized with the primer. The mutant primer used for performing nucleic acid amplification may correspond to either forward or reverse primer, and the other primer may have an arbitrary sequence. Alternatively, both the forward and reverse primers may be mutant primers.

EXAMPLES

The present invention will hereinafter be described in detail with examples; however, the present invention is not limited to the following examples.

[Example 1] Selective Amplification of DNA Containing T790M and C797S Mutations in Exon 20 of EGFR Gene The DNA prepared for evaluation of the discriminatory power of the ASP designed according to the present invention were DNA containing T790M and C797S mutations in exon 20 of human EGFR gene (mutant DNA) and DNA without the two gene mutations (wild-type DNA). For the mutant DNA, plasmid DNA incorporating sequences (SEQ ID NO: 2, SEQ ID NOs: 3 and 4) including the respective gene mutations were prepared (consigned to Eurofins Genomics), and for the wild-type DNA, a genomic DNA extracted and purified from K562 cell line was used.

SEQ ID NO: 2 is a sequence including the T790M mutation of EGFR gene, with codon 790 underlined and the single nucleotide polymorphism site indicated by boldface. SEQ ID NOs: 3 and 4 are sequences in the same region as SEQ ID NO: 2 of EGFR gene and include respective different C797S mutations. Codon 797 is underlined, and the single nucleotide polymorphism sites are indicated by boldface. SEQ ID NO: 1 is a portion of the wild-type sequence in the same region as SEQ ID NOs: 2 to 4 of EGFR gene.

(portion of wild-type sequence of EGFR gene)
[Chem 1]
SEQ ID NO: 1
ACTCAAGATCGCATTCATGCGTCTTCACCTGGAAGGGTCCATGTGCCCC

TCCTTCTGGCCACCATGCGAAGCCACACTGACGTGCCTCTCCCTCCCTCC

AGGAAGCCTACGTGATGGCCAGCGTGGACAACCCCCACGTGTGCCGCCTG

CTGGGCATCTGCCTCACCTCCACCGTGCAGCTCATCACGCAGCTCATGCC

CTTCGGCTGCCTCCTGGACTATGTCCGGGAACACAAAGACAATATTGGCT

CCCAGTACCTCCTCAACTGGTGTGTGCAGATCGCAAAGGTAATCAGGCAA

GGGAGATACGGGGAGGGGAGATAAGGAGCCAGGATCCTCACATGCGGTCT

GCGCTCCTGG (T790M mutant sequence of EGFR gene; [ATG] fragment)
[Chem 2]
SEQ ID NO: 2
ACTCAAGATCGCATTCATGCGTCTTCACCTGGAAGGGGTCCATGTGCCCC

TCCTTCTGGCCACCATGCGAAGCCACACTGACGTGCCTCTCCCTCCCTCC

AGGAAGCCTACGTGATGGCCAGCGTGGACAACCCCCACGTGTGCCGCCTG

CTGGGCATCTGCCTCACCTCCACCGTGCAGCTCATCATGCAGCTCATGCC

CTTCGGCTGCCTCCTGGACTATGTCCGGGAACACAAAGACAATATTGGCT

CCCAGTACCTGCTCAACTGGTGTGTGCAGATCGCAAAGGTAATGAGGGAA

GGGAGATACGGGGAGGGGAGATAAGGAGCCAGGATCCTCACATGCGGTCT

GCGCTCCTGG (C797S mutant sequence of EGFR gene; [AGC] fragment)
[Chem 3]
SEQ ID NO: 3
ACTCAAGATCGCATTCATGCGTCTTCACCTGGAAGGGGTCCATGTGCCCC

TCCTTCTGGCCACCATGCGAAGCCACACTGACGTGCCTCTCCCTCCCTCC

AGGAAGCCTACGTGATGGCCAGCGTGGACAACCCCCACGTGTGCCGCCTG

CTGGGCATCTGCCTCACCTCCACCGTGCAGCTCATCACGCAGCTCATGCC

CTTCGGCAGCCTCCTGGACTATGTCCGGGAACACAAAGACAATATTGGCT

CCCAGTACCTGCTCAACTGGTGTGTGCAGATCGCAAAGGTAATCAGGGAA

GGGAGATACGGGGAGGGGAGATAAGGAGCCAGGATCCTCAGATGCGGTCT

GCGCTCCTGG (C797S mutant sequence of EGFR gene; [TCC] fragment)
[Chem 4]
SEQ ID NO: 4
ACTCAAGATCGCATTCATGCGTCTTCACCTGGAAGGGGTCCATGTGCCCC

TCCTTCTGGCCACCATGCGAAGCCACACTGACGTGCCTCTCCCTCCCTCC

AGGAAGCCTACGTGATGGCCAGCGTGGACAACCCCCACGTGTGCCGCCTG

CTGGGCATCTGCCTCACCTCCACCGTGCAGCTCATCACGCAGCTCATGCC

CTTCGGCTCCCTCCTGGACTATGTCCGGGAACACAAAGACAATATTGGCT

CCCAGTACCTGCTCAACTGGTGTGTGCAGATCGCAAAGGTAATCAGGGAA

GGGAGATACGGGGAGGGGAGATAAGGAGCCAGGATCCTCACATGCGGTCT

GCGCTCCTGG (1) Primers for Detecting T790M and C797S Mutations in Exon 20 of EGFR Gene Synthesis of oligonucleotides having base sequences shown in SEQ ID NOs: 5 to 8 (hereinafter referred to as Primers 1 to 4) was consigned to a DNA synthesis service provider (Sigma-Aldrich LLC).

Primer 1 has a sequence complementary to one strand (the complementary strand of SEQ ID NO: 2) of a mutant nucleic acid containing codon 790 of human EGFR gene, the base (T) of the third nucleotide from the 3' end thereof corresponding to the single nucleotide polymorphism site, but has a base (C) which is the base of the second nucleotide from the 3' end and is not complementary to the base of the corresponding nucleotide of the strand (i.e., Primer 1 is hybridized to the complementary strand of SEQ ID NO: 2 with a mismatch of one base).

Primer 2 has a sequence complementary to one strand (the strand of SEQ ID NO: 4) of a mutant nucleic acid containing codon 797 of human EGFR gene, the base (G) of the third nucleotide from the 3' end thereof corresponding to the single nucleotide polymorphism site shown in SEQ ID NO: 4, but has a base (T) which is the base of the second nucleotide from the 3' end and is not complementary to the base of the corresponding nucleotide of the strand (i.e., Primer 2 is hybridized to the strand of SEQ ID NO: 4 with a mismatch of one base). Furthermore, Primer 2 has a sequence complementary to one strand (the strand of SEQ ID NO: 3) of a mutant nucleic acid containing codon 797 of human EGFR gene, the base (T) of the second nucleotide from the 3' end thereof corresponding to the single nucleotide polymorphism site shown in SEQ ID NO: 3, but has a base (G) which is the base of the third nucleotide from the 3' end and is not complementary to the base of the corresponding nucleotide of the strand (i.e., Primer 2 is hybridized to the strand of SEQ ID NO: 3 with a mismatch of one base). Primer 2 has a sequence complementary to one strand (the strand of SEQ ID NO: 1) of a wild-type nucleic acid containing codon 797 of human EGFR gene, but has bases (GT) which are the third and second nucleotides from the 3' end and are not complementary to the bases of the corresponding nucleotides of the strand (i.e., Primer 2 is hybridized to the strand of SEQ ID NO: 1 with a mismatch of two bases).

Primer 3 is a reverse primer paired with Primer 1, and Primer 4 is a forward primer paired with Primer 2. The bases corresponding to the single nucleotide polymorphism sites of Primers 1 and 2 are indicated by boldface, and the bases not complementary to the bases of the corresponding nucleotides of the strands to be hybridized with the primers are underlined.

(Primer 1)
[Chem 5]
SEQ ID NO: 5
5'-CCGTGCAGCTCATCATCC-3'

(Primer 2)
[Chem 6]
SEQ ID NO: 6
5'-GGAGATAGTCCAGGAGGGTG-3' (when hybridized to the strand of SEQ ID NO: 4)

5'-GGACATAGTCCAGGAGGGTG-3' (when hybridized to the strand of SEQ ID NO: 3)

5'-GGACATAGTCCAGGAGGGTG-3' (when hybridized to the strand of SEQ ID NO: 1)

(Primer 3)
[Chem 7]
SEQ ID NO: 7
5'-GGGAGCCAATATTGTCTTTGTG-3'

(Primer 4)
[Chem 8]
SEQ ID NO: 8
5'-ATGCGAAGCCACACTGAC-3'

(2) Analysis of T790M and C797S Mutations in Exon 20 of EGFR Gene by ASP-PCR Method (a) Reagents and Amplification Conditions A 25 μL reaction solution containing the following reagents was prepared and two-step real-time PCR analysis was performed using CFX96 (Bio-Rad).

TABLE 1

| | |
|---|---|
| 5x buffer (for Q5) | 5 μL |
| 10 mM dNTP | 0.5 μL |
| 10 μM forward primer | 1.25 μL |
| 10 μM reverse primer | 1.25 μL |
| 20x EvaGreen (registered trademark) | 1.25 μL |
| 2000 U/mL Q5 DNA polymerase (New England Biolabs Japan Inc.) | 0.25 μL |
| Nuclease-free Water | 10.5 μL |
| DNA specimen (7500 copies of linear plasmid DNA cleaved with appropriate restriction enzyme or 25 ng of extracted DNA) | 5 μL |
| Amplification condition | |
| 98° C. for 30 seconds | |
| 98° C. for 10 seconds, 64° C. for 30 seconds (40 cycles) | |

The results are shown in FIGS. 1 and 2. When the primers designed according to the present invention were used, no significant amplification from the wild-type DNA was recognized until 40 cycles, and the mutant DNA was selectively amplifiable (the mutant DNA was discriminable from the wild-type DNA). Particularly, in the case of codon 797 of EGFR gene, two forms of mutations can selectively be amplified at the same time with one primer, which is efficient.

[Example 2] Selective Amplification from DNA Containing G719A, G719S, and G719C Mutations in Exon 18 of EGFR Gene DNA prepared for evaluation of the discriminatory power of the ASP designed according to the present invention were DNA (mutant DNA) containing three kinds of mutations (G719A, G719S, G719C) at codon 719 in exon 18 of human EGFR gene and DNA (wild-type DNA) without the three gene mutations. For the mutant DNA, plasmid DNA incorporating sequences (SEQ ID NOs: 10, 11, and 12) including the respective gene mutations were prepared (consigned to Eurofins Genomics), and for the wild-type DNA, a genomic DNA extracted and purified from K562 cell line was used as in Example 1.

SEQ ID NOs: 10, 11, and 12 are sequences including the G719A mutation, the G719S mutation, and the G719C mutation, respectively, of EGFR gene, with the codon 719 underlined and the single nucleotide polymorphism sites indicated by boldface. SEQ ID NOs: 10, 11, and 12 are all sequences in the same region of EGFR gene. SEQ ID NO: 9 is a portion of the wild-type sequence in the same region as SEQ ID NOs: 10 to 12 of EGFR gene.

(portion of wild-type sequence of EGFR gene)
[Chem 9]
SEQ ID NO: 9
GTAGAGAAGGCGTACATTTGTCCTTCCAAATGAGCTGGCAAGTGCCGTGT

CCTGGCACCCAAGCCCATGCCGTGGCTGCTGGTCCCCCTGCTGGGCCATG

TCTGGCACTGCTTTCCAGCATGGTGAGGGCTGAGGTGACCCTTGTCTCTG

TGTTCTTGTCCCCCCCAGCTTGTGGAGCCTCTTACACCCAGTGGAGAAGC

TCCCAACCAAGCTCTCTTGAGGATCTTGAAGGAAACTGAATTCAAAAAGA

TCAAAGTGCTGGGCTCCGGTGCGTTCGGCACGGTGTATAAGGTAAGGTCC

CTGGCACAGGCCTCTGGGCTGGGCCGCAGGGCCTCTCATGGTCTGGTGGG

GAGCCCAGAGTCCTTGCAAGCTGTATATTTCCATCATCTACTTTACTCTT (G719A mutant sequence of EGFR gene; [GCC] fragment)
[Chem 10]
SEQ ID NO: 10
GTAGAGAAGGCGTACATTTGTCCTTCCAAATGAGCTGGCAAGTGCCGTGT

CCTGGCACCCAAGCCCATGCCGTGGCTGCTGGTCCCCCTGCTGGGCCATG

TCTGGCACTGCTTTCCAGCATGGTGAGGGCTGAGGTGACCCTTGTCTCTG

TGTTCTTGTCCCCCCCAGCTTGTGGAGCCTCTTACACCCAGTGGAGAAGC

TCCCAACCAAGCTCTCTTGAGGATCTTGAAGGAAACTGAATTCAAAAAGA

TCAAAGTGCTGGCCTCCGGTGCGTTCGGCACGGTGTATAAGGTAAGGTCC

CTGGCACAGGCCTCTGGGCTGGGCCGCAGGGCCTCTCATGGTCTGGTGGG

GAGCCCAGAGTCCTTGCAAGCTGTATATTTCCATCATCTACTTTACTCTT

-continued (G719S mutant sequence of EGFR gene; [AGC] fragment)
[Chem 11]

SEQ ID NO: 11
GTAGAGAAGGCGTACATTTGTCCTTCCAAATGAGCTGGCAAGTGCCGTGT

CCTGGCACCCAAGCCCATGCCGTGGCTGCTGGTCCCCCTGCTGGGCCATG

TCTGGCACTGCTTTCCAGCATGGTGAGGGCTGAGGTGACCCTTGTCTCTG

TGTTCTTGTCCCCCCCAGCTTGTGGAGCCTCTTACACCCAGTGGAGAAGC

TCCCAACCAAGCTCTCTTGAGGATCTTGAAGGAAACTGAATTCAAAAAGA

TCAAAGTGCTGAGCTCCGGTGCGTTCGGCACGGTGTATAAGGTAAGGTCC

CTGGCACAGGCCTCTGGGCTGGGCCGCAGGGCCTCTCATGGTCTGGTGGG

GAGCCCAGAGTCCTTGCAAGCTGTATATTTCCATCATCTACTTTACTCTT (G719C mutant sequence of EGFR gene; fragment)
[Chem 12]

SEQ ID NO: 12
GTAGAGAAGGCGTACATTTGTCCTTCCAAATGACCTGGCAAGTGCCGTGT

CCTGGCACCCAAGCCCATGCCGTGGCTGCTGGTCCCCCTGCTGGGCCATG

TCTGGCACTGCTTTCCAGCATGGTGAGGGCTGAGGTGACCCTTGTCTCTG

TGTTCTTGTCCCCCCCAGCTTGTGGAGCCTCTTACACCCAGTGGAGAAGC

TCCCAACCAAGCTCTCTTGAGGATCTTGAAGGAAACTGAATTCAAAAACA

TCAAAGTGCTGTGCTCCGGTGCGTTCGGCACGGTGTATAAGGTAAGGTCC

CTGGCACAGGCCTCTGGGCTGGGCCGCAGGGCCTCTCATGGTCTGGTGGG

GAGCCCAGAGTCCTTGCAAGCTGTATATTTCCATCATCTACTTTACTCTT (1) Primers for Detecting G719A, G719S, and G719C Mutations in Exon 18 of EGFR Gene Synthesis of oligonucleotides having base sequences shown in SEQ ID NOs: 13 to 15 (hereinafter referred to as Primers 5 to 7) was consigned to a DNA synthesis service provider (Sigma-Aldrich LLC).

Primer 5 has a sequence complementary to one strand (the strand of SEQ ID NO: 10) of a mutant nucleic acid containing codon 719 of human EGFR gene, the base (G) of the third nucleotide from the 3' end thereof corresponding to the single nucleotide polymorphism site of the G719A mutation, but has a nucleotide (T) which is the second nucleotide from the 3' end the base of which is not complementary to the base of the corresponding nucleotide of the strand (i.e., Primer 5 is hybridized to the strand of SEQ ID NO: 10 with a mismatch of one base). Furthermore, Primer 5 has a sequence complementary to one strand (the strand of SEQ ID NO: 11) of a mutant nucleic acid containing codon 719 of human EGFR gene, the base (T) of the second nucleotide from the 3' end thereof corresponding to the single nucleotide polymorphism site of the G719S mutation, but has a nucleotide (G) which is the third nucleotide from the 3' end the base of which is not complementary to the base of the corresponding nucleotide of the strand (i.e., Primer 5 is hybridized to the strand of SEQ ID NO: 11 with a mismatch of one base). Primer 5 has a sequence complementary to one strand (the strand of SEQ ID NO: 12) of a mutant nucleic acid containing codon 719 of human EGFR gene, but has bases (GT) which are the bases of the third and second nucleotides from the 3' end and are not complementary to the bases of the corresponding nucleotides of the strand (i.e., Primer 5 is hybridized to the strand of SEQ ID NO: 12 with a mismatch of two bases). Primer 5 has a sequence complementary to one strand (the strand of SEQ ID NO: 9) of a wild-type nucleic acid containing codon 719 of human EGFR gene, but has bases (GT) which are the third and second nucleotides from the 3' end and are not complementary to the bases of the corresponding nucleotides of the strand (i.e., Primer 5 is hybridized to the strand of SEQ ID NO: 9 with a mismatch of two bases).

Primer 6 has a sequence complementary to one strand (the strand of SEQ ID NO: 10) of a mutant nucleic acid containing codon 719 of human EGFR gene, the base (G) of the third nucleotide from the 3' end thereof corresponding to the single nucleotide polymorphism site of the G719A mutation, but has a nucleotide (A) which is the second nucleotide from the 3' end the base of which is not complementary to the base of the corresponding nucleotide of the strand (i.e., Primer 6 is hybridized to the strand of SEQ ID NO: 10 with a mismatch of one base). Furthermore, Primer 6 has a sequence complementary to one strand (the strand of SEQ ID NO: 12) of a mutant nucleic acid containing codon 719 of human EGFR gene, the base (A) of the second nucleotide from the 3' end thereof corresponding to the single nucleotide polymorphism site of the G719C mutation, but has a nucleotide (G) which is the third nucleotide from the 3' end the base of which is not complementary to the base of the corresponding nucleotide of the strand (i.e., Primer 6 is hybridized to the strand of SEQ ID NO: 12 with a mismatch of one base). Primer 6 has a sequence complementary to one strand (the strand of SEQ ID NO: 11) of a mutant nucleic acid containing codon 719 of human EGFR gene, but has bases (GA) which are the bases of the third and second nucleotides from the 3' end and are not complementary to the bases of the corresponding nucleotides of the strand (i.e., Primer 6 is hybridized to the strand of SEQ ID NO: 11 with a mismatch of two bases). Primer 6 has a sequence complementary to one strand (the strand of SEQ ID NO: 9) of a wild-type nucleic acid containing codon 719 of human EGFR gene, but has bases (GA) which are the bases of the third and second nucleotides from the 3' end and are not complementary to the bases of the corresponding nucleotides of the strand (i.e., Primer 6 is hybridized to the strand of SEQ ID NO: 9 with a mismatch of two bases).

Primer 7 is a common forward primer paired with primers 5 and 6. The bases corresponding to the single nucleotide polymorphism sites of primers 5 and 6 are indicated by boldface, and the bases not complementary to the bases of the corresponding nucleotides of the strands to be hybridized with the primers are underlined.

(Primer 5)
[Chem 13]

SEQ ID NO: 13
5'-CGAACGCACCGGAGGTC-3' (when hybridized to the strand of SEQ ID NO: 10)

5'-CGAACGCACCGGAGGTC-3' (when hybridized to the strand of SEQ ID NO: 11)

5'-CGAACGCACCGGAGGTC-3' (when hybridized to the strands of SEQ ID NOs: 12 and 9)

(primer 6)
[Chem 14]

SEQ ID NO: 14
5'-CGAACGCACCGGAGGAC-3' (when hybridized to the strand of SEQ ID NO: 10)

5'-CGAACGCACCGGAGGAC-3' (when hybridized to the strand of SEQ ID NO: 12)

5'-CGAACGCACCGGAGGAC-3' (when hybridized to the strands of SEQ ID NOs: 11 and 9)

(primer 7)
[Chem 15]

SEQ ID NO: 15
5'-AGCTCTCTTGAGGATCTTGAAGG-3'

(2) Analysis of G719A, G719S, and G719C Mutations in Exon 18 of EGFR Gene by ASP-PCR Method (a) Reagents and Amplification Conditions The analysis was performed under the same conditions as Example 1.

The results are shown in FIGS. 3 and 4. When the primers designed according to the present invention were used, no significant amplification from the wild-type DNA was recognized until 40 cycles, and the mutant DNA was selectively amplifiable (specific mutant DNA was discriminable from the wild-type DNA and another mutant DNA). Particularly, in the case of codon 719 of EGFR gene, three forms of mutations can selectively be amplified with two kinds of primers, which is efficient.

[Example 3] Selective Amplification of Codons 12, 13 in Exon 2 of KRAS Gene

As shown in Table 2, it is known that six kinds of point mutations occur at codons 12 and 13 in exon 2 of human KRAS gene. There are three each mutation forms in which the first or second base is respectively mutated among three bases constituting the codon, and therefore, when the ASP is designed according to the present invention by combining the respective forms, the number of primers for detecting 12 patterns of mutations at codons 12 and 13 is reduced to half, i.e., six kinds of primers, so that selective amplification can be achieved, which contributes to simplification and labor saving of detection reagents and operations.

TABLE 2

| | Codon 12 | | Codon 13 | |
|---|---|---|---|---|
| | A.A. Chng. | Base Seq. | A.A. Chng. | Base Seq. |
| WT | G12 | GGT | G13 | GGC |
| Mut | G12S | AGT | G13S | AGC |
| | G12R | CGT | G13R | CGC |
| | G12C | TGT | G13C | TGC |
| | G12D | GAT | G13D | GAC |
| | G12A | GCT | G13A | GCC |
| | G12V | GTT | G13V | GTC |

A.A. Chng.: Amino Acid Change
Base Seq.: Base Sequence
WT: Wild type
Mut: Mutant Plasmid DNAs incorporating respective genetic mutation sequences (SEQ ID NOs: 17 to 28) (consigned to Eurofins Genomics) as well as a gene sequence absent of the two gene mutations as the wild type (SEQ ID NO: 16) were prepared, and the discriminatory power of the ASP designed according to the present invention was evaluated.

(codon 12 mutant sequence [GGT] and codon 13 mutant
sequence [GGC] in exon 2 of KRAS gene; common fragment)
[Chem 16]

SEQ ID NO: 16
GGTACTGGTGGAGTATTTGATAGTGTATTAACCTTATGTGTGACATGTTCTAATATAGTCACAT

TTTCATTATTTTTATTATAAGGCCTGCTGAAAATGACTGAATATAAACTTGTGGTAGTTGGAGC

TGGTGGCGTAGGCAAGAGTGGCTTGACGATACAGCTAATTCAGAATCATTTTGTGGACGAATAT

GATCCAACAATAGAGGTAAATCTTGTTTTAATATGCATATTACTGGTGCAGGACCATTCTTTGA

TACAGATAAAGG (codon 12 mutant sequence in exon 2 of KRAS gene; G12S
[AGT] fragment)
[Chem 17]

SEQ ID NO: 17
GGTACTGGTGGAGTATTTGATAGTGTATTAACCTTATGTGTGACATGTTCTAATATAGTCACAT

TTTCATTATTTTTATTATAAGGCCTGCTGAAAATGACTGAATATAAACTTGTGGTAGTTGGAGC

TAGTGGCGTAGGCAAGAGTGCCTTGACGATACAGCTAATTCAGAATCATTTTGTGGACGAATAT

GATCCAACAATAGAGGTAAATCTTGTTTTAATATGCATATTACTGGTGCAGGACCATTCTTTGA

TACAGATAAAGG (codon 12 mutant sequence in exon 2 of KRAS gene; G12R
[CGT] fragment)
[Chem 18]

SEQ ID NO: 18
GGTACTGGTGGAGTATTTGATAGTGTATTAACCTTATGTGTGACATGTTCTAATATAGTCACAT

TTTCATTATTTTTATTATAAGGCCTGCTGAAAATGACTGAATATAAACTTGTGGTAGTTGGAGC

TCGTGGCGTAGGCAAGAGTGCCTTGACGATACAGCTAATTCAGAATCATTTTGTGGACGAATAT

GATCCAACAATAGAGGTAAATCTTGTTTTAATATGCATATTACTGGTGCAGGACCATTCTTTGA

TACAGATAAAGG (codon 12 mutant sequence in exon 2 of KRAS gene; G12C fragment)
[Chem 19]

SEQ ID NO: 19

GGTACTGGTGGAGTATTTGATAGTGTATTAACCTTATGTGTGACATGTTCTAATATAGTCACAT

TTTCATTATTTTTATTATAAGGCCTGCTGAAAATGACTGAATATAAACTTGTGGTAGTTGGAGC

TTGTGGCGTAGGCAAGAGTGCCTTGACGATACAGCTAATTCAGAATCATTTTGTGGACGAATAT

GATCCAACAATAGAGGTAAATCTTGTTTTAATATGCATATTACTGGTGCAGGACCATTCTTTGA

TACAGATAAAGG (codon 12 mutant sequence in exon 2 of KRAS gene; G12D [GAT] fragment)
[Chem 20]

SEQ ID NO: 20

GGTACTGGTGGAGTATTTGATAGTGTATTAACCTTATGTGTGACATGTTCTAATATAGTCACAT

TTTCATTATTTTTATTATAAGCCCTGCTGAAAATGACTGAATATAAACTTGTGGTAGTTGGAGC

TGATGGCGTAGGCAAGAGTGCCTTGACGATACAGCTAATTCAGAATCATTTTGTGGACGAATAT

GATCCAACAATAGAGGTAAATCTTGTTTTAATATGCATATTACTGGTGCAGGACCATTCTTTGA

TACAGATAAAGG (codon 12 inutant sequence in exon 2 of KRAS gene; G12A [GCT] fragment)
[Chem 21]

SEQ ID NO: 21

GGTACTGGTGGAGTATTTGATAGTGTATTAACCTTATGTGTGACATGTTCTAATATAGTCACAT

TTTCATTATTTTTATTATAAGGCCTGCTGAAAATGACTGAATATAAACTTGTGGTAGTTGGAGC

TGCTGGCGTAGGCAAGAGTGCCTTGACGATACAGCTAATTCAGAATCATTTTGTGGACGAATAT

GATCCAACAATAGAGGTAAATCTTGTTTTAATATGCATATTACTGGTGCAGGACCATTCTTTGA

TACAGATAAAGG (codon 12 mutant sequence in exon 2 of KRAS gene; G12V [GTT] fragment)
[Chem 22]

SEQ ID NO: 22

GGTACTGGTGGAGTATTTGATAGTGTATTAACCTTATGTGTGACATGTTCTAATATAGTCACAT

TTTCATTATTTTTATTATAAGGCCTGCTGAAAATGACTGAATATAAACTTGTGGTAGTTGGAGC

TGTTGGCGTAGGCAAGAGTGCCTTGACGATACAGCTAATTCAGAATCATTTTGTGGACGAATAT

GATCCAACAATAGAGGTAAATCTTGTTTTAATATGCATATTACTGGTGCAGGACCATTCTTTGA

TACAGATAAAGG (codon 13 mutant sequence in exon 2 of KRAS gene; G13S [AGC] fragment)
([Chem 23]

SEQ ID NO: 23

GGTACTGGTGGAGTATTTGATAGTGTATTAACCTTATGTGTGAGATGTTCTAATATAGTCACAT

TTTCATTATTTTTATTATAAGGCCTGCTGAAAATGACTGAATATAAACTTGTGGTAGTTGGAGC

TGGTAGCGTAGGCAAGAGTGCCTTGACGATACAGCTAATTCAGAATCATTTTGTGGACGAATAT

GATCCAACAATAGAGGTAAATCTTGTTTTAATATGCATATTACTGGTGCAGGACCATTCTTTGA

TACAGATAAAGG (codon 13 mutant sequence in exon 2 of KRAS gene; G13R [CGC] fragment)
[Chem 24]

SEQ ID NO: 24

GGTACTGGTGGAGTATTTGATAGTGTATTAACCTTATGTGTGACATGTTCTAATATAGTCAGAT

TTTCATTATTTTTATTATAAGGCCTGCTGAAAATGACTGAATATAAACTTGTGGTAGTTGGAGC

```
TGGTCGCGTAGGCAAGAGTGCCTTGACGATACAGCTAATTCAGAATCATTTTGTGGACGAATAT

GATCCAACAATAGAGGTAAATCTTGTTTTAATATGCATATTACTGGTGCAGGACCATTCTTTGA

TACAGATAAAGG (codon 13 mutant sequence in exon 2 of KRAS gene; G13C
fragment)
[Chem 25]
                                                            SEQ ID NO: 25
GGTACTGGTGGAGTATTTGATAGTGTATTAACCTTATGTGTGACATGTTCTAATATAGTCACAT

TTTCATTATTTTTATTATAAGGCCTGCTGAAAATGACTGAATATAAACTTGTGGTAGTTGGAGC

TGGTTGCGTAGGCAAGAGTGCCTTGACGATACAGCTAATTCAGAATCATTTTGTGGACGAATAT

GATCCAACAATAGAGGTAAATCTTGTTTTAATATGCATATTACTGGTGCAGGACCATTCTTTGA

TACAGATAAAGG (codon 13 mutant sequence in exon 2 of KRAS gene; G13D
[GAC] fragment)
[Chem 26]
                                                            SEQ ID NO: 26
GGTACTGGTGGAGTATTTGATAGTGTATTAACCTTATGTGTGACATGTTCTAATATAGTCACAT

TTTCATTATTTTTATTATAAGGCCTGCTGAAAATGACTGAATATAAACTTGTGGTAGTTGGAGC

TGGTGACGTAGGCAAGAGTGCCTTGACGATACAGCTAATTCAGAATCATTTTGTGGACGAATAT

GATCCAACAATAGAGGTAAATCTTGTTTTAATATGCATATTACTGGTGCAGGACCATTCTTTGA

TACAGATAAAGG (codon 13 mutant sequence in exon 2 of KRAS gene; G13A
[GCC] fragment)
[Chem 27]
                                                            SEQ ID NO: 27
GGTACTGGTGGAGTATTTGATAGTGTATTAACCTTATGTGTGACATGTTCTAATATAGTCACAT

TTTCATTATTTTTATTATAAGGCCTGCTGAAAATGACTGAATATAAACTTGTGGTAGTTGGAGC

TGGTGCCGTAGGCAAGAGTGCCTTGACGATACAGCTAATTCAGAATCATTTTGTGGACGAATAT

GATCCAACAATAGAGGTAAATCTTGTTTTAATATGGATATTACTGGTGCAGGACCATTCTTTGA

TACAGATAAAGG (codon 13 mutant sequence in exon 2 of KRAS gene; G13V
[GTC] fragment)
[Chem 28]
                                                            SEQ ID NO: 28
GGTACTGGTGGAGTATTTGATAGTGTATTAACCTTATGTGTGACATGTTCTAATATAGTCACAT

TTTCATTATTTTTATTATAAGGCCTGCTGAAAATGACTGAATATAAACTTGTGGTAGTTGGAGC

TGGTGTCGTAGGCAAGAGTGCCTTGACGATACAGCTAATTCAGAATCATTTTGTGGACGAATAT

GATCCAACAATAGAGGTAAATCTTGTTTTAATATGCATATTACTGGTGCAGGACCATTCTTTGA

TACAGATAAAGG
```

(1) Primers for Detecting Codon 12 and Codon 13 Mutations in Exon 2 of KRAS Gene Synthesis of oligonucleotides having the base sequences shown in SEQ ID NOs: 29 to 35 (hereinafter referred to as Primers 8 to 14) was consigned to a DNA synthesis service provider (Sigma-Aldrich LLC).

Primer 8 has a sequence complementary to G12S and G12D mutant nucleic acid at codon 12 in exon 2 of human KRAS gene, has a nucleotide (T) which is the third nucleotide from the 3' end thereof, the base of which being complementary to a mutant nucleotide at the G12D nucleotide polymorphism site, the nucleotide though being in a noncomplementary relationship at the G12S, but has a nucleotide (T) which is the second nucleotide from the 3' end thereof, the base of which being not complementary to G12D, the nucleotide though being complementary to a G12S nucleotide polymorphism site (A).

Primer 9 has a sequence complementary to G12R and G12A mutant nucleic acid at codon 12 in exon 2 of human KRAS gene, has a nucleotide (G) which is the third nucleotide from the 3' end thereof, the base of which being complementary to a mutant nucleotide at the G12A nucleotide polymorphism site, the nucleotide though being in a noncomplementary relationship at the G12R, but has a nucleotide (G) which is the second nucleotide from the 3' end thereof, the base of which being not complementary to G12A, the nucleotide though being complementary to a G12R nucleotide polymorphism site (C).

Primer 10 has a sequence complementary to G12C and G12V mutant nucleic acid at codon 12 in exon 2 of human KRAS gene, has a nucleotide (A) which is the third nucleotide from the 3' end thereof, the base of which being complementary to a mutant nucleotide at the G12V nucleotide polymorphism site, the nucleotide though being in a noncomplementary relationship at the G12C, but has a nucleotide (A) which is the second nucleotide from the 3' end thereof, the base of which being not complementary to G12V, the nucleotide though being complementary to a G12C nucleotide polymorphism site (T).

Primer 11 has a sequence complementary to G13S and G13A mutant nucleic acid at codon 13 in exon 2 of human KRAS gene, has a nucleotide (G) which is the third nucleotide from the 3' end thereof, the base of which being complementary to a mutant nucleotide at the G13A nucleotide polymorphism site, the nucleotide though being in a noncomplementary relationship at the G13S, but has a nucleotide (T) which is the second nucleotide from the 3' end thereof, the base of which being not complementary to G13A, the nucleotide though being complementary to a G13S nucleotide polymorphism site (A).

Primer 12 has a sequence complementary to G13R and G13V mutant nucleic acid at codon 13 in exon 2 of human KRAS gene, has a nucleotide (A) which is the third nucleotide from the 3' end thereof, the base of which being complementary to a mutant nucleotide at the G13V nucleotide polymorphism site, the nucleotide though being in a noncomplementary relationship at the G13R, but has a nucleotide (G) which is the second nucleotide from the 3' end thereof, the base of which being not complementary to G13V, the nucleotide though being complementary to a G13R nucleotide polymorphism site (C).

Primer 13 has a sequence complementary to G13C and G13D mutant nucleic acid at codon 13 in exon 2 of human KRAS gene, has a nucleotide (T) which is the third nucleotide from the 3' end thereof, the base of which being complementary to a mutant nucleotide at the G13D nucleotide polymorphism site, the nucleotide though being in a noncomplementary relationship at the G13C, but has a nucleotide (A) which is the second nucleotide from the 3' end thereof, the base of which being not complementary to G13D, the nucleotide though being complementary to a G13C nucleotide polymorphism site (T).

Primer 14 is a common forward primer paired with Primers 8 to 13.

(Primer 8)
[Chem 29]
SEQ ID NO: 29
5'-CTCTTGCCTACGCCATTA-3'

(Primer 9)
[Chem 30]
SEQ ID NO: 30
5'-TCTTGCCTACGCCAGGA-3'

(Primer 10)
[Chem 31]
SEQ ID NO: 31
5'-CTCTTGCCTACGCCAAAA-3'

(Primer 11)
[Chem 32]
SEQ ID NO: 32
5'-GCACTCTTGCCTACGGTA-3'

(Primer 12)
[Chem 33]
SEQ ID NO: 33
5'-GCACTCTTGCCTACGAGA-3'

(Primer 13)
[Chem 34]
SEQ ID NO: 34
5'-GCACTCTTGCCTACGTAA-3'

(Primer 14)
[Chem 35]
SEQ ID NO: 35
5'-AAACTTGTGGTAGTTGGAGC-3'

(2) Analysis of Mutations at Codons 12 and 13 in Exon 2 of KRAS Gene by ASP-PCR Method
(a) Reagents and Amplification Conditions A 25 µL reaction solution containing the following reagents was prepared and two-step real-time PCR analysis was performed with CFX96 (Bio-Rad).

TABLE 3

| | |
|---|---|
| 5x buffer (for Q5) | 5 µL |
| 10 mM dNTP | 0.5 µL |
| 10 µM forward primer [SEQ ID NO: 35] | 1.25 µL |
| 10 µM reverse primer [SEQ ID NOs: 29 to 34] | 1.25 µL |
| 20x EvaGreen | 1.25 µL |
| 2000 U/mL Q5 DNA polymerase | 0.25 µL |
| Nuclease-free Water | 10.5 µL |
| DNA specimen | 5 µL |
| (Linear plasmid DNA [SEQ ID NOs: 16 to 28] cleaved with appropriate restriction enzyme: 7500 copies) | |
| Amplification condition | |
| 98° C. for 30 seconds | |
| 98° C. for 10 seconds, 62° C. for 30 seconds (40 cycles) | |

The results for codon 12 are shown in FIGS. 5 to 7, and the results for codon 13 are shown in FIGS. 8 to 10. When the primers designed according to the present invention are used, no amplification from the wild type was observed, and it can be said that the mutant can specifically be amplified. Particularly, in the case of KRAS gene, the number of primers for detecting 12 patterns of mutations at codons 12 and 13 is reduced to half so that selective amplification can be achieved with six kinds of primers, which contributes to simplification and labor saving of detection reagents and operations.

INDUSTRIAL APPLICABILITY

The primer according to the primer designing method of the present invention can be used for a genetic diagnosis using a biological sample, a genetic diagnosis reagent, a pedigree analysis method, a pedigree analysis reagent, a plant variety identification method, a plant variety identification reagent, a meat breed judgment method, a meat breed judgment method reagent, a forensic analysis method, a forensic analysis reagent, etc.

The invention claimed is:

1. A method for detecting single base substitutions in a nucleic acid containing two adjacent single nucleotide polymorphism (SNP) sites by utilizing a polymerase chain reaction, the method comprising the steps of:
   (a) hybridizing to the nucleic acid a mutant primer in which the position of the third nucleotide from the 3' end of the mutant primer corresponds to the position of the first single nucleotide polymorphism,
      the base of the second nucleotide from the 3' end of the mutant primer is not complementary to the base of the nucleotide of the corresponding position in the first template nucleic acid having a mutant nucleotide of the first single nucleotide polymorphism,
      the base of the other nucleotides of the mutant primer are complementary to the bases of the nucleotides of the corresponding positions in the first template nucleic acid,
      the position of the second nucleotide from the 3' end of the mutant primer corresponds to the position of the second single nucleotide polymorphism,
      the base of the third nucleotide from the 3' end of the mutant primer is not complementary to the base of the nucleotide of the corresponding position in the second template nucleic acid having a mutant nucleotide of the second single nucleotide polymorphism, and
      the bases of the other nucleotides of the mutant primer are complementary to the bases of the nucleotides of the corresponding positions in the second template nucleic acid;
   (b) elongating the mutant primer with a DNA polymerase and deoxyribonucleoside triphosphate that is a substrate thereof; and
   (c) determining that the mutant primer is elongated based on the presence of an amplification product of the polymerase chain reaction, and thereby, detecting the single base substitutions contained in the nucleic acid based on elongation of the mutant primer.

2. A method for amplifying a fragment of polynucleotides comprising the steps of:
   (i) hybridizing a first primer and a second primer to a first deoxyribonucleic acid (DNA) molecule containing the first single nucleotide polymorphism (SNP) site and a second DNA molecule containing the second SNP site, wherein the two SNP sites are adjacent to each other;
   (ii) elongating the first primer and the second primer with a DNA polymerase in the presence of deoxyribonucleoside triphosphate;
   (iii) hybridizing the second primer to the elongated first primer and hybridizing the first primer to the elongated second primer;
   (iv) elongating the second primer hybridized to the elongated first primer and the first primer hybridized to the elongated second primer in the presence of deoxyribonucleoside triphosphate with a DNA polymerase; and
   (v) optionally repeating the steps (iii) and (iv) once to 50 times,
   wherein
   the nucleotide sequence of the first primer except for one position of the nucleotides is complementary to a second strand of the first DNA molecule, and
   the nucleotide sequence of the first primer except for one position of the nucleotides is complementary to a second strand of the second DNA molecule,
   the position of the third nucleotide from the 3' end of the first primer corresponds to the position of the first single nucleotide polymorphism on the first DNA molecule, whereas the base of the second nucleotide from the 3' end of the first primer is not complementary to the base of the nucleotide of the corresponding position in the second strand of the first DNA molecule, and
      the position of the second nucleotide from the 3' end of the first primer-corresponds to the position of the second single nucleotide polymorphism on the second DNA molecule, whereas the base of the third nucleotide from the 3' end of the first primer is not complementary to the base of the nucleotide of the corresponding position in the second strand of the second DNA molecule,
   wherein
   the nucleotide sequence of the second primer is complementary to a first strand of the first DNA molecule, and
   the nucleotide sequence of the second primer is complementary to a first strand of the second DNA molecule.

3. The method for detecting single base substitutions according to claim 1, wherein each single base substitutions are two adjacent single base substitutions of EGFR gene, KRAS gene, or NRAS gene.

* * * * *

SEQUENCE LISTING

<160> NUMBER OF SEQ ID NOS: 35

<210> SEQ ID NO 1

```
<211> LENGTH: 360
<212> TYPE: DNA
<213> ORGANISM: Homo sapiens

<400> SEQUENCE: 1
actcaagatc gcattcatgc gtcttcacct ggaaggggtc catgtgcccc tccttctggc      60
caccatgcga agccacactg acgtgcctct ccctccctcc aggaagccta cgtgatggcc     120
agcgtggaca accccacgt gtgccgcctg ctgggcatct gcctcacctc caccgtgcag     180
ctcatcacgc agctcatgcc cttcggctgc ctcctggact atgtccggga acacaaagac     240
aatattggct cccagtacct gctcaactgg tgtgtgcaga tcgcaaaggt aatcagggaa     300
gggagatacg gggaggggag ataaggagcc aggatcctca catgcggtct gcgctcctgg     360

<210> SEQ ID NO 2
<211> LENGTH: 360
<212> TYPE: DNA
<213> ORGANISM: Homo sapiens
<220> FEATURE:
<221> NAME/KEY: mutation
<222> LOCATION: (188)..(188)
<223> OTHER INFORMATION: T790M amino acid substitution

<400> SEQUENCE: 2
actcaagatc gcattcatgc gtcttcacct ggaaggggtc catgtgcccc tccttctggc      60
caccatgcga agccacactg acgtgcctct ccctccctcc aggaagccta cgtgatggcc     120
agcgtggaca accccacgt gtgccgcctg ctgggcatct gcctcacctc caccgtgcag     180
ctcatcatgc agctcatgcc cttcggctgc ctcctggact atgtccggga acacaaagac     240
aatattggct cccagtacct gctcaactgg tgtgtgcaga tcgcaaaggt aatcagggaa     300
gggagatacg gggaggggag ataaggagcc aggatcctca catgcggtct gcgctcctgg     360

<210> SEQ ID NO 3
<211> LENGTH: 360
<212> TYPE: DNA
<213> ORGANISM: Homo sapiens
<220> FEATURE:
<221> NAME/KEY: mutation
<222> LOCATION: (208)..(208)
<223> OTHER INFORMATION: C797S amino acid substitution

<400> SEQUENCE: 3
actcaagatc gcattcatgc gtcttcacct ggaaggggtc catgtgcccc tccttctggc      60
caccatgcga agccacactg acgtgcctct ccctccctcc aggaagccta cgtgatggcc     120
agcgtggaca accccacgt gtgccgcctg ctgggcatct gcctcacctc caccgtgcag     180
ctcatcacgc agctcatgcc cttcggcagc ctcctggact atgtccggga acacaaagac     240
aatattggct cccagtacct gctcaactgg tgtgtgcaga tcgcaaaggt aatcagggaa     300
gggagatacg gggaggggag ataaggagcc aggatcctca catgcggtct gcgctcctgg     360

<210> SEQ ID NO 4
<211> LENGTH: 360
<212> TYPE: DNA
<213> ORGANISM: Homo sapiens
<220> FEATURE:
<221> NAME/KEY: mutation
<222> LOCATION: (209)..(209)
<223> OTHER INFORMATION: C797S amino acid substitution

<400> SEQUENCE: 4
actcaagatc gcattcatgc gtcttcacct ggaaggggtc catgtgcccc tccttctggc      60
```

```
caccatgcga agccacactg acgtgcctct ccctccctcc aggaagccta cgtgatggcc      120
agcgtggaca accccacgt gtgccgcctg ctgggcatct gcctcacctc caccgtgcag       180
ctcatcacgc agctcatgcc cttcggctcc ctcctggact atgtccggga acacaaagac     240
aatattggct cccagtacct gctcaactgg tgtgtgcaga tcgcaaaggt aatcagggaa     300
gggagatacg gggaggggag ataaggagcc aggatcctca catgcggtct gcgctcctgg    360
```

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5

```
ccgtgcagct catcatcc                                                    18
```

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6

```
ggacatagtc caggagggtg                                                  20
```

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7

```
gggagccaat attgtctttg tg                                               22
```

<210> SEQ ID NO 8
<211> LENGTH: 18
<212> TYPE: DNA
<213> ORGANISM: Artificial Sequence
<220> FEATURE:
<223> OTHER INFORMATION: primer

<400> SEQUENCE: 8

```
atgcgaagcc acactgac                                                    18
```

<210> SEQ ID NO 9
<211> LENGTH: 400
<212> TYPE: DNA
<213> ORGANISM: Homo sapiens

<400> SEQUENCE: 9

```
gtagagaagg cgtacatttg tccttccaaa tgagctggca agtgccgtgt cctggcaccc      60
aagcccatgc cgtggctgct ggtccccctg ctgggccatg tctggcactg ctttccagca    120
tggtgagggc tgaggtgacc cttgtctctg tgttcttgtc cccccagct tgtggagcct     180 cttacaccca gtggagaagc tcccaaccaa gctctcttga ggatcttgaa ggaaactgaa    240
ttcaaaaaga tcaaagtgct gggctccggt gcgttcggca cggtgtataa ggtaaggtcc    300
ctggcacagg cctctgggct gggccgcagg gcctctcatg gtctggtggg gagcccagag    360
```

```
tccttgcaag ctgtatattt ccatcatcta ctttactctt              400
```

<210> SEQ ID NO 10
<211> LENGTH: 400
<212> TYPE: DNA
<213> ORGANISM: Homo sapiens
<220> FEATURE:
<221> NAME/KEY: mutation
<222> LOCATION: (263)..(263)
<223> OTHER INFORMATION: G719A amino acid substitution

<400> SEQUENCE: 10

```
gtagagaagg cgtacatttg tccttccaaa tgagctggca agtgccgtgt cctggcaccc    60
aagcccatgc cgtggctgct ggtccccctg ctgggccatg tctggcactg ctttccagca   120
tggtgagggc tgaggtgacc cttgtctctg tgttcttgtc ccccccagct tgtggagcct   180
cttacaccca gtggagaagc tcccaaccaa gctctcttga ggatcttgaa ggaaactgaa   240
ttcaaaaaga tcaaagtgct ggcctccggt gcgttcggca cggtgtataa ggtaaggtcc   300
ctggcacagg cctctgggct gggccgcagg gcctctcatg gtctggtggg gagcccagag   360
tccttgcaag ctgtatattt ccatcatcta ctttactctt                         400
```

<210> SEQ ID NO 11
<211> LENGTH: 400
<212> TYPE: DNA
<213> ORGANISM: Homo sapiens
<220> FEATURE:
<221> NAME/KEY: mutation
<222> LOCATION: (262)..(262)
<223> OTHER INFORMATION: G719S amino acid substitution

<400> SEQUENCE: 11

```
gtagagaagg cgtacatttg tccttccaaa tgagctggca agtgccgtgt cctggcaccc    60
aagcccatgc cgtggctgct ggtccccctg ctgggccatg tctggcactg ctttccagca   120
tggtgagggc tgaggtgacc cttgtctctg tgttcttgtc ccccccagct tgtggagcct   180
cttacaccca gtggagaagc tcccaaccaa gctctcttga ggatcttgaa ggaaactgaa   240
ttcaaaaaga tcaaagtgct gagctccggt gcgttcggca cggtgtataa ggtaaggtcc   300
ctggcacagg cctctgggct gggccgcagg gcctctcatg gtctggtggg gagcccagag   360
tccttgcaag ctgtatattt ccatcatcta ctttactctt                         400
```

<210> SEQ ID NO 12
<211> LENGTH: 400
<212> TYPE: DNA
<213> ORGANISM: Homo sapiens
<220> FEATURE:
<221> NAME/KEY: mutation
<222> LOCATION: (262)..(262)
<223> OTHER INFORMATION: G719C amino acid substitution

<400> SEQUENCE: 12

```
gtagagaagg cgtacatttg tccttccaaa tgagctggca agtgccgtgt cctggcaccc    60
aagcccatgc cgtggctgct ggtccccctg ctgggccatg tctggcactg ctttccagca   120
tggtgagggc tgaggtgacc cttgtctctg tgttcttgtc ccccccagct tgtggagcct   180
cttacaccca gtggagaagc tcccaaccaa gctctcttga ggatcttgaa ggaaactgaa   240
ttcaaaaaga tcaaagtgct gtgctccggt gcgttcggca cggtgtataa ggtaaggtcc   300
ctggcacagg cctctgggct gggccgcagg gcctctcatg gtctggtggg gagcccagag   360
tccttgcaag ctgtatattt ccatcatcta ctttactctt                         400
```

```
<210> SEQ ID NO 13
<211> LENGTH: 17
<212> TYPE: DNA
<213> ORGANISM: Artificial Sequence
<220> FEATURE:
<223> OTHER INFORMATION: primer

<400> SEQUENCE: 13
cgaacgcacc ggaggtc                                                   17

<210> SEQ ID NO 14
<211> LENGTH: 17
<212> TYPE: DNA
<213> ORGANISM: Artificial Sequence
<220> FEATURE:
<223> OTHER INFORMATION: primer

<400> SEQUENCE: 14
cgaacgcacc ggaggac                                                   17

<210> SEQ ID NO 15
<211> LENGTH: 23
<212> TYPE: DNA
<213> ORGANISM: Artificial Sequence
<220> FEATURE:
<223> OTHER INFORMATION: primer

<400> SEQUENCE: 15
agctctcttg aggatcttga agg                                            23

<210> SEQ ID NO 16
<211> LENGTH: 268
<212> TYPE: DNA
<213> ORGANISM: Homo sapiens

<400> SEQUENCE: 16
ggtactggtg gagtatttga tagtgtatta accttatgtg tgacatgttc taatatagtc    60
acattttcat tattttattt ataaggcctg ctgaaaatga ctgaatataa acttgtggta   120
gttggagctg gtggcgtagg caagagtgcc ttgacgatac agctaattca gaatcatttt   180
gtggacgaat atgatccaac aatagaggta aatcttgttt taatatgcat attactggtg   240
caggaccatt ctttgataca gataaagg                                      268

<210> SEQ ID NO 17
<211> LENGTH: 268
<212> TYPE: DNA
<213> ORGANISM: Homo sapiens
<220> FEATURE:
<221> NAME/KEY: mutation
<222> LOCATION: (130)..(130)
<223> OTHER INFORMATION: G12S amino acid substitution

<400> SEQUENCE: 17
ggtactggtg gagtatttga tagtgtatta accttatgtg tgacatgttc taatatagtc    60
acattttcat tattttattt ataaggcctg ctgaaaatga ctgaatataa acttgtggta   120
gttggagcta gtggcgtagg caagagtgcc ttgacgatac agctaattca gaatcatttt   180
gtggacgaat atgatccaac aatagaggta aatcttgttt taatatgcat attactggtg   240
caggaccatt ctttgataca gataaagg                                      268

<210> SEQ ID NO 18
```

```
<211> LENGTH: 268
<212> TYPE: DNA
<213> ORGANISM: Homo sapiens
<220> FEATURE:
<221> NAME/KEY: mutation
<222> LOCATION: (130)..(130)
<223> OTHER INFORMATION: G12R amino acid substitution

<400> SEQUENCE: 18
ggtactggtg gagtatttga tagtgtatta accttatgtg tgacatgttc taatatagtc    60
acattttcat tattttttatt ataaggcctg ctgaaaatga ctgaatataa acttgtggta   120
gttggagctc gtggcgtagg caagagtgcc ttgacgatac agctaattca gaatcatttt   180
gtggacgaat atgatccaac aatagaggta aatcttgttt taatatgcat attactggtg   240
caggaccatt ctttgataca gataaagg                                      268

<210> SEQ ID NO 19
<211> LENGTH: 268
<212> TYPE: DNA
<213> ORGANISM: Homo sapiens
<220> FEATURE:
<221> NAME/KEY: mutation
<222> LOCATION: (130)..(130)
<223> OTHER INFORMATION: G12C amino acid substitution

<400> SEQUENCE: 19
ggtactggtg gagtatttga tagtgtatta accttatgtg tgacatgttc taatatagtc    60
acattttcat tattttttatt ataaggcctg ctgaaaatga ctgaatataa acttgtggta   120
gttggagctt gtggcgtagg caagagtgcc ttgacgatac agctaattca gaatcatttt   180
gtggacgaat atgatccaac aatagaggta aatcttgttt taatatgcat attactggtg   240
caggaccatt ctttgataca gataaagg                                      268

<210> SEQ ID NO 20
<211> LENGTH: 268
<212> TYPE: DNA
<213> ORGANISM: Homo sapiens
<220> FEATURE:
<221> NAME/KEY: mutation
<222> LOCATION: (131)..(131)
<223> OTHER INFORMATION: G12D amino acid substitution

<400> SEQUENCE: 20
ggtactggtg gagtatttga tagtgtatta accttatgtg tgacatgttc taatatagtc    60
acattttcat tattttttatt ataaggcctg ctgaaaatga ctgaatataa acttgtggta   120
gttggagctg atggcgtagg caagagtgcc ttgacgatac agctaattca gaatcatttt   180
gtggacgaat atgatccaac aatagaggta aatcttgttt taatatgcat attactggtg   240
caggaccatt ctttgataca gataaagg                                      268

<210> SEQ ID NO 21
<211> LENGTH: 268
<212> TYPE: DNA
<213> ORGANISM: Homo sapiens
<220> FEATURE:
<221> NAME/KEY: mutation
<222> LOCATION: (131)..(131)
<223> OTHER INFORMATION: G12A amino acid substitution

<400> SEQUENCE: 21
ggtactggtg gagtatttga tagtgtatta accttatgtg tgacatgttc taatatagtc    60
acattttcat tattttttatt ataaggcctg ctgaaaatga ctgaatataa acttgtggta   120
```
gttggagctg ctggcgtagg caagagtgcc ttgacgatac agctaattca gaatcatttt    180
gtggacgaat atgatccaac aatagaggta aatcttgttt taatatgcat attactggtg    240
caggaccatt ctttgataca gataaagg    268

<210> SEQ ID NO 22
<211> LENGTH: 268
<212> TYPE: DNA
<213> ORGANISM: Homo sapiens
<220> FEATURE:
<221> NAME/KEY: mutation
<222> LOCATION: (131)..(131)
<223> OTHER INFORMATION: G12V amino acid substitution

<400> SEQUENCE: 22
ggtactggtg gagtatttga tagtgtatta accttatgtg tgacatgttc taatatagtc    60
acattttcat tatttttatt ataaggcctg ctgaaaatga ctgaatataa acttgtggta    120
gttggagctg ttggcgtagg caagagtgcc ttgacgatac agctaattca gaatcatttt    180
gtggacgaat atgatccaac aatagaggta aatcttgttt taatatgcat attactggtg    240
caggaccatt ctttgataca gataaagg    268

<210> SEQ ID NO 23
<211> LENGTH: 268
<212> TYPE: DNA
<213> ORGANISM: Homo sapiens
<220> FEATURE:
<221> NAME/KEY: mutation
<222> LOCATION: (133)..(133)
<223> OTHER INFORMATION: G13S amino acid substitution

<400> SEQUENCE: 23
ggtactggtg gagtatttga tagtgtatta accttatgtg tgacatgttc taatatagtc    60
acattttcat tatttttatt ataaggcctg ctgaaaatga ctgaatataa acttgtggta    120
gttggagctg gtagcgtagg caagagtgcc ttgacgatac agctaattca gaatcatttt    180
gtggacgaat atgatccaac aatagaggta aatcttgttt taatatgcat attactggtg    240
caggaccatt ctttgataca gataaagg    268

<210> SEQ ID NO 24
<211> LENGTH: 268
<212> TYPE: DNA
<213> ORGANISM: Homo sapiens
<220> FEATURE:
<221> NAME/KEY: mutation
<222> LOCATION: (133)..(133)
<223> OTHER INFORMATION: G13R amino acid substitution

<400> SEQUENCE: 24
ggtactggtg gagtatttga tagtgtatta accttatgtg tgacatgttc taatatagtc    60
acattttcat tatttttatt ataaggcctg ctgaaaatga ctgaatataa acttgtggta    120
gttggagctg gtcgcgtagg caagagtgcc ttgacgatac agctaattca gaatcatttt    180
gtggacgaat atgatccaac aatagaggta aatcttgttt taatatgcat attactggtg    240
caggaccatt ctttgataca gataaagg    268

<210> SEQ ID NO 25
<211> LENGTH: 268
<212> TYPE: DNA
<213> ORGANISM: Homo sapiens
<220> FEATURE:

```
<221> NAME/KEY: mutation
<222> LOCATION: (133)..(133)
<223> OTHER INFORMATION: G13R amino acid substitution

<400> SEQUENCE: 25
ggtactggtg gagtatttga tagtgtatta accttatgtg tgacatgttc taatatagtc      60
acattttcat tattttatt ataaggcctg ctgaaaatga ctgaatataa acttgtggta     120
gttggagctg gttgcgtagg caagagtgcc ttgacgatac agctaattca gaatcatttt     180
gtggacgaat atgatccaac aatagaggta aatcttgttt taatatgcat attactggtg     240
caggaccatt ctttgataca gataaagg                                        268

<210> SEQ ID NO 26
<211> LENGTH: 268
<212> TYPE: DNA
<213> ORGANISM: Homo sapiens
<220> FEATURE:
<221> NAME/KEY: mutation
<222> LOCATION: (134)..(134)
<223> OTHER INFORMATION: G13D amino acid substitution

<400> SEQUENCE: 26
ggtactggtg gagtatttga tagtgtatta accttatgtg tgacatgttc taatatagtc      60
acattttcat tattttatt ataaggcctg ctgaaaatga ctgaatataa acttgtggta     120
gttggagctg gtgacgtagg caagagtgcc ttgacgatac agctaattca gaatcatttt     180
gtggacgaat atgatccaac aatagaggta aatcttgttt taatatgcat attactggtg     240
caggaccatt ctttgataca gataaagg                                        268

<210> SEQ ID NO 27
<211> LENGTH: 268
<212> TYPE: DNA
<213> ORGANISM: Homo sapiens
<220> FEATURE:
<221> NAME/KEY: mutation
<222> LOCATION: (134)..(134)
<223> OTHER INFORMATION: G13A amino acid substitution

<400> SEQUENCE: 27
ggtactggtg gagtatttga tagtgtatta accttatgtg tgacatgttc taatatagtc      60
acattttcat tattttatt ataaggcctg ctgaaaatga ctgaatataa acttgtggta     120
gttggagctg gtgccgtagg caagagtgcc ttgacgatac agctaattca gaatcatttt     180
gtggacgaat atgatccaac aatagaggta aatcttgttt taatatgcat attactggtg     240
caggaccatt ctttgataca gataaagg                                        268

<210> SEQ ID NO 28
<211> LENGTH: 268
<212> TYPE: DNA
<213> ORGANISM: Homo sapiens
<220> FEATURE:
<221> NAME/KEY: mutation
<222> LOCATION: (134)..(134)
<223> OTHER INFORMATION: G13V amino acid substitution

<400> SEQUENCE: 28
ggtactggtg gagtatttga tagtgtatta accttatgtg tgacatgttc taatatagtc      60
acattttcat tattttatt ataaggcctg ctgaaaatga ctgaatataa acttgtggta     120
gttggagctg gtgtcgtagg caagagtgcc ttgacgatac agctaattca gaatcatttt     180
gtggacgaat atgatccaac aatagaggta aatcttgttt taatatgcat attactggtg     240
```
caggaccatt ctttgataca gataaagg                                      268

<210> SEQ ID NO 29
<211> LENGTH: 18
<212> TYPE: DNA
<213> ORGANISM: Artificial Sequence
<220> FEATURE:
<223> OTHER INFORMATION: primer

<400> SEQUENCE: 29
ctcttgccta cgccatta                                                 18

<210> SEQ ID NO 30
<211> LENGTH: 17
<212> TYPE: DNA
<213> ORGANISM: Artificial Sequence
<220> FEATURE:
<223> OTHER INFORMATION: primer

<400> SEQUENCE: 30
tcttgcctac gccagga                                                  17

<210> SEQ ID NO 31
<211> LENGTH: 18
<212> TYPE: DNA
<213> ORGANISM: Artificial Sequence
<220> FEATURE:
<223> OTHER INFORMATION: primer

<400> SEQUENCE: 31
ctcttgccta cgccaaaa                                                 18

<210> SEQ ID NO 32
<211> LENGTH: 18
<212> TYPE: DNA
<213> ORGANISM: Artificial Sequence
<220> FEATURE:
<223> OTHER INFORMATION: primer

<400> SEQUENCE: 32
gcactcttgc ctacggta                                                 18

<210> SEQ ID NO 33
<211> LENGTH: 18
<212> TYPE: DNA
<213> ORGANISM: Artificial Sequence
<220> FEATURE:
<223> OTHER INFORMATION: primer

<400> SEQUENCE: 33
gcactcttgc ctacgaga                                                 18

<210> SEQ ID NO 34
<211> LENGTH: 18
<212> TYPE: DNA
<213> ORGANISM: Artificial Sequence
<220> FEATURE:
<223> OTHER INFORMATION: primer

<400> SEQUENCE: 34
gcactcttgc ctacgtaa                                                 18

<210> SEQ ID NO 35
<211> LENGTH: 20
<212> TYPE: DNA

```
<213> ORGANISM: Artificial Sequence
<220> FEATURE:
<223> OTHER INFORMATION: primer

<400> SEQUENCE: 35
aaacttgtgg tagttggagc                                              20
```